United States Patent
Dyke et al.

[11] Patent Number: 6,066,657
[45] Date of Patent: May 23, 2000

[54] BENZOFURAN-4-CARBOXAMIDES AND THEIR THERAPEUTIC USE

[75] Inventors: Hazel Joan Dyke; John Gary Montana; Christopher Lowe; Karen Ann Runcie; Alan Findlay Haughan; Verity Margaret Sabin; Duncan Hannah; Louise Picken; Andrew Sharpe, all of Cambridge, United Kingdom

[73] Assignee: Darwin Discovery, Ltd., United Kingdom

[21] Appl. No.: 09/246,335

[22] Filed: Feb. 9, 1999

[30] Foreign Application Priority Data

Feb. 9, 1998 [GB] United Kingdom ............ 9802748
Apr. 24, 1998 [GB] United Kingdom ............ 9808829

[51] Int. Cl.[7] ............ A61K 31/44; A61K 31/36
[52] U.S. Cl. ............ 514/337; 546/284.1; 514/466; 549/467
[58] Field of Search ............ 549/467; 514/466, 514/337; 546/284.1

[56] References Cited

FOREIGN PATENT DOCUMENTS

| | | |
|---|---|---|
| 0771794 | 5/1997 | European Pat. Off. |
| 9720833 | 6/1997 | WIPO. |
| 9744337 | 11/1997 | WIPO. |
| 9807715 | 2/1998 | WIPO. |

*Primary Examiner*—Amelia Owens
*Attorney, Agent, or Firm*—Saliwanchik, Lloyd & Saliwanchik

[57] ABSTRACT

A compound of formula (i)

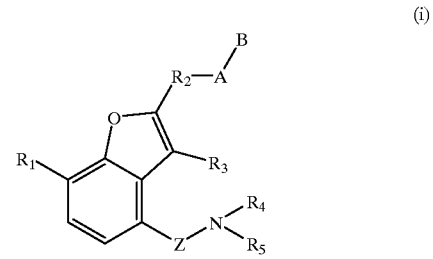

has therapeutic utility via inhibition of phosphodiesterase and THF release.

13 Claims, No Drawings

BENZOFURAN-4-CARBOXAMIDES AND THEIR THERAPEUTIC USE

FIELD OF THE INVENTION

The present invention relates to novel benzofuran compounds and to their formulation and use as pharmaceuticals.

BACKGROUND OF THE INVENTION

EP-A-0637586 describes benzofuran derivatives of acetylcholinesterase inhibitors. U.S. Pat. No. 4,910,193 discloses benzofuran amides for the treatment of serotonin-induced gastrointestinal disturbances. WO-A-9408962 discloses benzofuran derivatives as fibrinogen receptor antagonists.

WO-A-9744337, WO-A-9720883, EP-A-0771794 and WO-A-9807715 disclose benzofuran derivatives as selective phosphodiesterase (PDE) IV inhibitors. The modes of action of phosphodiesterases and also tumour necrosis factors (TNF), and the therapeutic utilities of inhibitors thereof, are described in WO-A-9636638 and U.S. Pat. No. 5,821,366, the contents of which are incorporated herein by reference.

SUMMARY OF THE INVENTION

This invention provides novel compounds having therapeutic utility, in particular for the treatment of disease states associated with proteins which mediate cellular activity, for example by inhibiting TNF and/or PDE IV. According to the invention, the compounds are of formula (i):

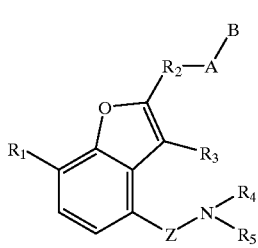

(i)

Z is CO or CS;

$R_1$ is OH, alkoxy optionally substituted with one or more halogens or thioalkyl optionally substituted with one or more halogens;

$R_3$ is H, alkyl or halogen;

$R_4$ is H or alkyl;

$R^5$ is aryl or heteroaryl either of which may be substituted at any position with (one or more) substituents $R_{14}$ or alkyl-$R_{14}$;

$R_{14}$ is alkyl optionally substituted with one or more halogens, aryl, heteroaryl, heterocyclo, $CO_2R_8$, $CONR_9R_{10}$, $SO_2NR_9R_{10}$, $OR_{11}$, halogen, CN, $NR_8R_{12}$, $COR_{13}$, $S(O)_pR_{13}$ or $NHSO_2CF_3^-$, p is 0–2;

$R_8$ is H, alkyl, cycloalkyl, aryl, heteroaryl, heterocyclo, cycloalkylalkyl, arylalkyl, heteroarylalkyl or heterocycloalkyl;

$R_9$ and $R_{10}$ are the same or different and are H, alkyl, cycloalkyl, aryl, heteroaryl, heterocyclo, cycloalkylalkyl, arylalkyl, heteroarylalkyl, heterocycloalkyl or $NR_9R_{10}$ represents a heterocyclic ring;

$R_{11}$ is H, alkyl (optionally substituted with one or more halogens), cycloalkyl, aryl, heteroaryl, heterocyclo, cycloalkylalkyl, arylalkyl, heteroarylalkyl or heterocycloalkyl;

$R_{12}$ is H, alkyl, cycloalkyl, aryl, heteroaryl, heterocyclo, cycloalkylalkyl, arylalkyl, heteroarylalkyl, heterocycloalkyl, alkylcarbonyl, alkoxycarbonyl, arylcarbonyl, heteroarylcarbonyl, heterocyclocarbonyl, alkylsulphonyl, arylsulphonyl, heteroarylsulphonyl or heterocyclosulphonyl;

$R_{13}$ is alkyl, cycloalkyl, aryl, heteroaryl, heterocyclo, cycloalkylalkyl, arylalkyl, heteroarylalkyl or heterocycloalkyl;

$R_2$ is alkyl, arylalkyl, cycloalkylalkyl, heteroarylalkyl or heterocycloalkyl, any of which is attached at any position on the alkyl portion to A and (through the same or a different position) to the benzofuran ring wherein the aryl or heteroaryl group is optionally substituted at any position by (one or more) substitutent $R_{14}$ or alkyl-$R_{14}$, and the cycloalkyl or heterocycloalkyl group is optionally substituted at any position with (one or more) substitutents $R_7$ or alkyl-$R_7$, or $R_2$ is absent;

A is —O—, —O—$(C(R_{15})_2)_n$—, —O—$(C(R_{15})_2)_n$—C(=O)—$(C(R_{15})_2)_m$—, —O—$(C(R_{15})_2)_n$—$SO_q$—$(C(R_{15})_2)_m$—, —$NR_6$—, —$NR_6$—$(C(R_{15})_2)_n$—, —$NR_6$—$(C(R_{15})_2)_n$—C(=O)—$(C(R_{15})_2)_m$—, —$NR_6$—$(C(R_{15})_2)_n$—$SO_q$—$(C(R_{15})_2)_m$—, —$SO_q$—, $SO_q$—$(C(R_{15})_2)_n$— or $SO_qNR_6$—;

$R_6$ is H or alkyl;

n is 1–4;

m is 0–4;

q is 1 or 2;

$R_{15}$ is H or alkyl;

$R_7$ is carbonyl oxygen (i.e. =O attached to a C atom), $CO_2R_8$, $CONR_9R_{10}$, $SO_2NR_9R_{10}$, $NR_8R_{12}$, $OR_{11}$, alkyl (optionally substituted with one or more halogens), halogen, CN, $NHSO_2CF_3$, tetrazolyl or heterocyclo;

when A is —O—, —O—$(C(R_{15})_2)_n$—, —O—$(C(R_{15})_2)_n$—C(=O)—$(C(R_{15})_2)_m$—, —$NR_6$—, —$NR_6$—$(C(R_{15})_2)_n$— or —$NR_6$—$(C(R_{15})_2)_n$—C(=O)—$(C(R_{15})_2)_m$—, then B is a heterocyclic ring (substituted at any position with (one or more) substitutents $R_7$ or alkyl-$R_7$), or alkyl, aryl or heteroaryl (any of which is substituted at any position with (one or more) substituents $R_{14}$ or alkyl-$R_{14}$);

when A is —O—$(C(R_{15})_2)_n$—$SO_q$—$(C(R_{15})_2)_m$—, —$NR_6$—$(C(R_{15})_2)_n$—$SO_q$—$(C(R_{15})_2)_m$—, —$SO_q$—, $SO_q$—$(C(R_5)_2)_m$—, or $SO_qNR_6$—; then B is a heterocyclic ring (optionally substituted at any position with (one or more) substituents $R_7$ or alkyl-$R_7$), or alkyl, aryl or heteroaryl (any of which is optionally substituted at any position with (one or more) substituents $R_{14}$ or alkyl-$R_{14}$);

when $R_2$ is cycloalkylalkyl, then B is a heterocyclic ring (optionally substituted at any position with (one or more) substitutents $R_7$ or alkyl-$R_7$), or alkyl, aryl or heteroaryl (any of which is optionally substituted at any position with (one or more) substituents $R_{14}$ or alkyl-$R_{14}$) for all A; and when $R_2$ is cycloalkylalkyl and A is —O—, B can also be H;

including N-oxides and pharmaceutically acceptable salts.

This invention provides also a method for mediating or inhibiting the enzymatic activity or catalytic activity of PDE IV in a mammal in need thereof and for inhibiting the production of TNF in a mammal in need thereof, which comprises administering to said mammal an effective amount of a compound of formula (i) or a pharmaceutically-acceptable salt thereof.

DESCRIPTION OF THE INVENTION

Suitable pharmaceutically-acceptable salts are pharmaceutically-acceptable base salts and pharmaceutically-acceptable acid addition salts. Certain of the compounds of formula (i) which contain an acidic group form base salts. Suitable pharmaceutically-acceptable base salts include metal salts, such as alkali metal salts, for example sodium salts, or organic amine salts such as that provided with ethylenediamine.

Certain of the compounds of formula (i) which contain a basic group form acid addition salts. Suitable acid addition salts include pharmaceutically-acceptable inorganic salts such as the sulphate, nitrate, phosphate, borate, hydrochloride and hydrobromide, and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (i) are prepared using conventional procedures.

It will be appreciated by those skilled in the art that some of the compounds of formula (i) may exist in more than one tautomeric or geometric form. This invention extends to all tautomeric forms.

It will be appreciated that the compounds according to the invention can contain one or more asymmetrically substituted carbon atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as a part of another group includes straight and branched chain alkyl groups containing up to 6 atoms. Alkoxy means an alkyl-O— group in which the alkyl group is as previously described, and thioalkyl means an alkyl-S— group. Cycloalkyl includes a non-aromatic cyclic or multicyclic ring system of 3 to 10 carbon atoms. The cyclic alkyl may optionally be partially unsaturated. Aryl indicates mono- or multicyclic carboxylic radicals containing 6 to 10 carbon atoms. Arylalkyl means an aryl-alkyl- group wherein the aryl and alkyl are as described herein. Heteroaryl means a 5 to 10 membered aromatic monocyclic or multicyclic hydrocarbon ring system in which one or more of the atoms in the ring system is an element other than carbon, chosen from amongst nitrogen, oxygen or sulphur. Heterocyclo means a 4 to 10 membered saturated or partially saturated monocyclic or multicyclic hydrocarbon ring system in which one or more of the atoms in the ring system is an element other than carbon, chosen from amongst nitrogen, oxygen or sulphur. Heteroarylalkyl means a heteroaryl-alkyl-group and heterocycloalkyl means a heterocycloalkyl- group. Alkylcarbonyl means an alkyl-CO— group in which the alkyl group is as previously described. Arylcarbonyl means an aryl-CO— group in which the aryl group is as previously described. Heteroarylcarbonyl means a heteroaryl-CO— group and heterocyclocarbonyl means a heterocyclo-CO— group. Arylsulphonyl means as aryl-SO$_2$— group in which the aryl group is as previously described. Heteroarylsulphonyl means a heteroaryl-SO$_2$-group and heterocyclosulphonyl means a heterocyclo-SO$_2$— group. Alkoxycarbonyl means an alkoxy-CO— group in which the alkoxy group is as previously described. Alkylsulphonyl means an alkyl-SO$_2$— group in which the alkyl group is as previously described. Carbonyl oxygen means a —CO— group. It will be appreciated that a carbonyl oxygen can not be a substituent on an aryl ring. Heterocyclic ring means a 4 to 10 membered monocyclic or multicyclic ring system (which may saturated or partially unsaturated) wherein one or more of the atoms in the ring system is an element other than carbon chosen from amongst nitrogen, oxygen or sulphur atoms. Halogen means fluorine, chlorine, bromine or iodine.

The invention further provides a process for the preparation of a compound of formula (i), in which $R_1$–$R_{15}$, m, n, p, q, A and B are as defined above. It will be appreciated that functional groups such as amino, hydroxyl or carboxyl groups present in the various compounds described below, and which it is desired to retain, may need to be in protected forms before any reaction is initiated. In such instances, removal of the protecting group may be the final step in a particular reaction. Suitable protecting groups for such functionality will be apparent to those skilled in the art. For specific details, see Protective Groups in Organic Synthesis, Wiley Interscience, T W Greene.

Thus, a process for preparing compounds of formula (i) in which B contains an —OH group comprises of deprotecting (for example by hydrogenolysis or hydrolysis) a compound of formula (i) in which B contains an appropriate —OP wherein P represents a suitable protecting group (e.g. benzyl or acetyl).

A process for the preparation of a compound of formula (i) comprises reaction of an appropriate carboxylic acid of formula (ii) with a suitable amine of formula (iii)

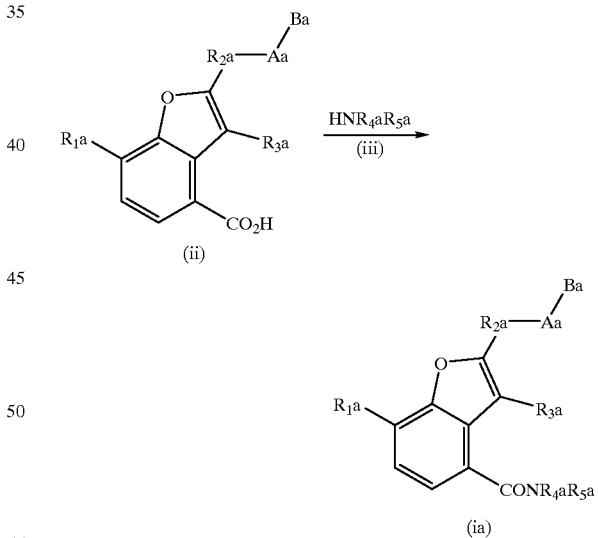

wherein $R_1$a represents $R_1$ as defined in relation to formula (i) or a group convertable to $R_1$ and $R_2$a–$R_5$a similarly represent $R_2$–$R_5$ or groups convertable to $R_2$–$R_5$ respectively and Aa represents A or a group convertable to A and Ba represents B or a group convertable to B; and thereafter, if required, converting any group $R_1$a to $R_1$ and/or $R_2$a to $R_2$ and/or $R_{3a}$ to $R_3$ and/or $R_4$a to $R_4$ and/or $R_5$a to $R_5$ and/or Aa to A and/or Ba to B. The reaction of a carboxylic acid of formula (ii) with an amine of formula (iii) may be carried out under any suitable conditions known to those skilled in the art. Favourably the carboxylic acid is converted into an acid chloride, mixed anhydride, p-nitrophenyl ester or other activated intermediate prior to reaction with an amine of formula (iii). Favourably the reaction with the amine of formula (iii) is carried out in the presence of a suitable base, for example an amine such as triethylamine, preferably in an appropriate solvent such as dichloromethane. In some cases a stronger base, such a sodium hydride, and a polar solvent such as dimethylformamide, will be required.

Carboxylic acids of formula (ii) are either commercially available, previously described compounds or are prepared using standard procedures known to those skilled in the art. For example, a carboxylic acid of formula (ii) is conveniently prepared from an appropriate benzofuran of formula (v). Conversion of a benzofuran of formula (v) to a carboxylic acid of formula (ii) can be carried out using any standard procedures known to those skilled in the art. For example, a benzofuran of formula (v) can be formulated to provide an aldehyde of formula (iv), which can then be oxidised to provide the corresponding acid of formula (ii). Alternatively, a benzofuran of formula (v) can be brominated to provide a bromide of formula (vi), which can then be converted into a carboxylic acid of formula (ii), for example by organometal-catalysed carboxylation or by generation of a Grignard reagent followed by quenching with carbon dioxide.

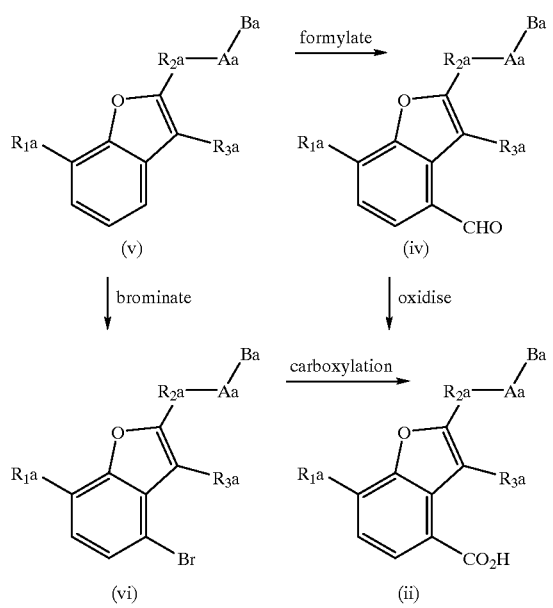

Benzofurans of formula (v) may be prepared by any standard procedure known to those skilled in the art, for example by the procedures described in WO-A-9720833 or by treatment of a compound of formula (vii) with a strong base (such as butyllithium) followed by reaction of an agent BaAaR$_2$aW where W is a suitable leaving group such as a halogen, or an agent G$_1$, where G$_1$ contains for example, a reactive carbonyl moiety, a nitrile or a sulfonyl moiety and after reaction constitutes the group BaAaR$_2$a. Alternatively, benzofurans of formula (v) may be prepared from compounds of formula (viii) by modification of the group Aa, for example by the formation of a sulfonyl chloride from a sulfinic acid salt using N-chlorosuccinimide and subsequent treatment with a reactive species Ba, for example dimethylamine. Compounds of the formula (viii) may be prepared by treatment of a compound of formula (vii) with a strong base (such as butyllithium) followed by reaction of an agent AaR$_2$aW where W is suitable leaving group such as a halogen, or an agent G$_2$, where G$_2$ contains for example, a reactive carbonyl moiety, a nitrile or a sulfonyl moiety and after reaction constitutes the group AaR$_2$a. A compound of formula (vii) may be prepared by any standard procedure known to those skilled in the art, for example by procedures similar to those described in Organic Syntheses, Coll. Vol. V, 251–254.

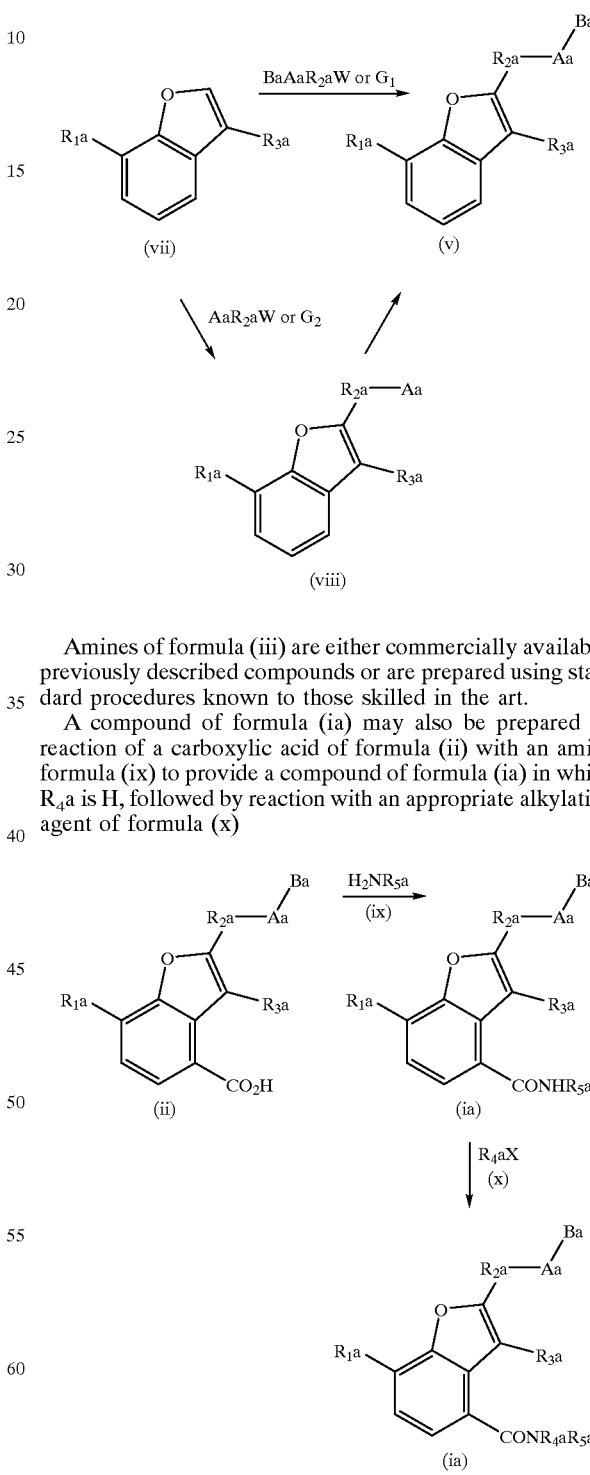

Amines of formula (iii) are either commercially available, previously described compounds or are prepared using standard procedures known to those skilled in the art.

A compound of formula (ia) may also be prepared by reaction of a carboxylic acid of formula (ii) with an amine formula (ix) to provide a compound of formula (ia) in which R$_4$a is H, followed by reaction with an appropriate alkylating agent of formula (x)

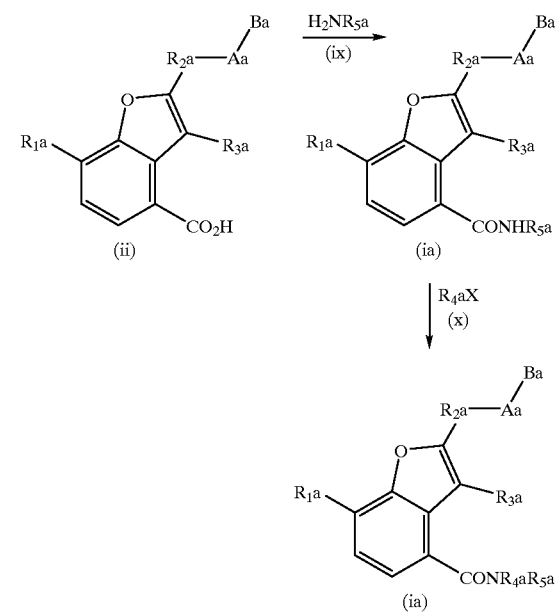

wherein R$_1$a–R$_5$a, Aa and Ba are as defined earlier and X represents a suitable leaving group such as a halogen. The reaction of a carboxylic acid of formula (ii) with an amine of formula (ix) may be carried out under any suitable conditions known to those skilled in the art. Favourably, the carboxylic acid is converted into an acid chloride, mixed anhydride, p-nitrophenyl ester or other activated intermediate prior to reaction with an amine of formula (ix). Favourably, the reaction with the amine of formula (ix) is carried out in the presence of a suitable base, for example an amine such as triethylamine, preferably in an appropriate solvent such as dichloromethane. In some cases a stronger base such as sodium hydride, and a polar solvent such as dimethylformamide, may be required.

The reaction of a compound of formula (ia) in which $R_4$ is H with an alkylating agent of formula (x) may be carried out under any suitable conditions known to those skilled in the art. Favourably the reaction is carried out using an appropriate base, such as sodium hydride, preferably in an appropriate solvent such a dimethylformamide. Amines of formula (ix) and alkylating agents of formula (x) are either commercially available or are prepared using standard procedures known to those skilled in the art.

Some compounds of formula (i) may be prepared from other compounds of formula (i). For example, compounds in which A—B contains an alkoxy group may be prepared from compounds in which A—B contains a hydroxy group by alkylation using any suitable conditions known to those skilled in the art. Suitable conditions include the use of an appropriate base such as sodium hydride in an appropriate solvent such as DMF, followed by the addition of a suitable alkyl halide such as iodomethane.

Compounds in which A—B contains an amino group can be prepared by reductive amination of an appropriate carbonyl-containing compound.

Compounds of formula (i) in which $R_5$ contains a pyridyl-N-oxide may be prepared from compounds of formula (i) in which $R_5$ contains a pyridyl group using any standard conditions known to those skilled in the art. Suitable conditions include the use of an oxidising agent such as peracetic acid in an appropriate solvent such as chloroform.

It will be appreciated by those skilled in the art that is some cases it may more appropriate to carry out the above mentioned transformations on compounds of formula (ii), (vi), or (v) rather than on compounds of formula (i).

It will be appreciated that where a particular stereoisomer of formula (i) is required, this may be obtained by conventional resolution techniques such as high performance liquid chromatography or the synthetic processes herein described may by performed using the appropriate homochiral starting material.

The invention includes the prevention and treatment of TNF mediated disease or disease states, by which is meant any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biological responses and binds to the same cellular receptor, both TNF-α and TNF-β are considered to be inhibited by compounds of the present invention and thus are herein referred to collectively as "TNF" unless specifically delineated otherwise.

PDE IV inhibitors are useful in the treatment of a variety of allergic and inflammatory diseases, including: asthma, chronic bronchitis, chronic pulmonary inflammatory disease, chronic obstructure pulmonary disease, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (alzheimer's disease), memory impairment associated with Parkinson's disease, depression and multi-infarct demential. PDE IV inhibitors are also useful in conditions ameliorated by neuroprotectant activity, such as cardiac arrest, stroke and intermittent claudication. PDE IV inhibitors may be useful in the treatment of tarditive dyskinesia, ischaemia and Huntingdon's disease. Additionally, PDE IV inhibitors may have utility as gastroprotectants. A special embodiment of the therapeutic methods of the present invention is the treatment of asthma.

TNF release inhibitors are useful in the treatment of viral infections. The viruses contemplated for treatment herein are those that produce TNF as a result of infection, or those which are sensitive to inhibition, such as by decreases replication, directly or indirectly, by the TNF release inhibitors of Formula (i). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex.*

This invention more specifically relates to a method of treatment a mammal, afflicted with a human immunodeficiency virus (HIV), which comprises administering to such mammal an effective TNF release-inhibiting amount of a compound of Formula (i) or a pharmaceutically-acceptable salt thereof.

The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease sate for treatment is fungal meningitis.

The compounds of formula (i) are preferably in pharmaceutically-acceptable form. By pharmaceutically-acceptable form is means, inter alia, a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%. When used herein the term "pharmaceutically-acceptable" encompasses materials suitable for both human and veterinary use.

A compound of formula (i) or where appropriate a pharmaceutically-acceptable salt thereof and/or pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous intramuscular, intrasternal injection or infusion techniques. In addition to the treatment of warm-blooded animals such as mice, rats, horses, cattle, sheep, dogs, cats, etc, the compound of the invention are effective in the treatment of humans.

The compositions of the invention may be in the form of tablets, capsules, sachets, vials, powders, granules, lozenges, suppositories, reconstitutable powders, or liquid preparations such as oral or sterile parental solutions or suspension. Topical formulations are also envisages where appropriate.

In order to obtain consistency of administration it is preferred that a composition of the invention is in the form of a unit dose. Unit dose presentation forms for oral administration may be tablets and capsules and may contain conventional excipients such a binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinyl pyrrolidone, sodium starch glycollate or microcrystalline cellulose; or pharmaceutically-acceptable wetting agents such as sodium lauryl sulphate.

Solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practise, in particular with an enteric coating.

Oral liquid preparations may be in the form of, for example, emulsions, syrups or elixirs, or may be presented as s dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 $\mu$m, such as from 0.1 to 50 $\mu$m, preferably less than 10 $\mu$m, for example from 1 to 10 $\mu$m, 1 to 5 $\mu$m or from 2 to 5 $\mu$m. Where appropriate, small amounts of other anti-asthmatics and bronchodilators for example sympathomimetic amines such a isoprenaline, isoetharine, salbutamol, phenylephrine and ephadrine; corticosteroids such a prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions, the compound can be dissolved in water for injection and filter-sterilised before filling into a suitable vial or ampoule and sealing.

Advantageously, adjuvants such as a local anaesthetic, a preservation and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or is appropriate a pharmaceutically-acceptable salt thereof, are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (i), or if appropriate a pharmaceutically-acceptable salt thereof, will compromise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than one a day, for example 2, 3, 4, 5 or 6 times a day, but preferably 1 to 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

The following Examples illustrate the invention.

INTERMEDIATE 1

Cyclopropyl-(7-methoxybenzofuran-2-yl)-methanone

To a stirred solution of 7-methoxybenzofuran (3.0 g) in tetrahydrofuran (60 ml) cooled to −78° C. under an atmosphere of nitrogen was added dropwise n-butyllithium (1.6M in hexanes, 15.2 ml). After stirring at −78° C. for 30 minutes, magnesium bromide diethyl etherate (6.3 g) was added in single portion and the reaction mixture allowed to warm to 0° C. and stirred for 30 minutes. Cyclopropyl cyanide (1.8 ml) was then added dropwise and the mixture allowed to warm slowly to room temperature and stirred for 18 h. Aqueous hydrochloric acid (2M, 50 ml) was added to the reaction mixture and stirring continued for 1 h. The mixture was extracted with ethyl acetate (250 ml), then washed successively with water (50 ml) and brine (50 ml). The organic layer was separated and dried over magnesium sulfate, filtered and concentrated in vacuo. Purification by flash chromatography on silica eluting with 5–20% ethyl acetate in hexane afforded the title compound as a yellow oil (0.96 g).

TLC $R_f$ 0.41 (20% ethyl acetate in hexane)

INTERMEDIATE 2

Cyclopropyl-(7-methoxybenzofuran-2-yl)-methanol

To a stirred solution of 7-methoxybenzofuran (2.0 g) in tetrahydrofuran (30 ml) cooled to −60° C. under an atmosphere of nitrogen was added dropwise n-butyllithium (1.6M in hexanes, 8.9 ml). After stirring at −60° C. for 10 minutes, magnesium bromide diethyl etherate (3.8 g) was added in single portion and the reaction mixture stirred at −50° C. for 10 minutes. After cooling to −78° C., cyclopropane carboxaldehyde (1.0 ml) was added in a single portion and the mixture allowed to warm slowly to room temperature and stirred for 1 h. Water (2 ml) was added and the tetrahydrofuran removed in vacuo. The residue was partitioned between ethyl acetate (50 ml) and water (50 ml); the aqueous layer was extracted with ethyl acetate (50 ml); the organic layers were combined, dried over magnesium sulfate, filtered and concentrated in vacuo. Purification by flash chromatography on silica eluting with 0–5% methanol in dichloromethane afforded the title compound as a yellow gum (1.88 g).

TLC $R_f$ 0.14 (dichloromethane)

INTERMEDIATE 3

2-(Cyclopropyl-methoxy-methyl)-7-methoxybenzofuran

To a stirred suspension of sodium hydride (60% dispersion in mineral oil, 0.52 g) in tetrahydrofuran (60 ml) under an atmosphere of nitrogen was added slowly a solution of cyclopropyl-(7-methoxybenzofuran-2-yl)-methanol (1.88 g) in tetrahydrofuran (15 ml). After stirring for 5 minutes, iodomethane (1.6 ml) was added and the mixture concentrated in vacuo. The residue was partitioned between ethyl acetate (100 ml) and water (100 ml), the organic layer washed with water (100 ml), separated, dried over magnesium sulfate, filtered and concentrated in vacuo. Purification by flash chromatography on silica eluting with dichloromethane afforded the title compound as a yellow gum (1.62 g).

TLC $R_f$ 0.78 (dichloromethane)

INTERMEDIATE 4

7-Methoxybenzofuran-2-sulfinic Acid, Lithium Salt n-butyllithium (1.6M in hexanes, 4.6 ml) was added dropwise to a stirred solution of 7-methoxybenzofuran (1 g) in tetrahydrofuran (10 ml) at −78° C. under an inert atmosphere. After stirring for a further 15 minutes sulfur dioxide was bubbled through for 10 minutes, until the reaction showed acidic pH on damp indicator paper. Hexane (40 ml) was added and the reaction warmed to room temperature. The precipitate was filtered and washed with hexane (50 ml) to yield the title compound as a tan solid (1.2 g).

Mass spectrum 211 [M-1] free acid

INTERMEDIATE 5

7-Methoxy-2-methylsulfanylbenzofuran n-Butyllithium (1.6M in hexanes, 10.2 ml) was added dropwise to a cooled (−78° C.) solution of 7-methoxybenzofuran (2.0 g) in tetrahydrofuran (40 ml) under an inert atmosphere. Methyl disulfide (1.46 ml) was added and the reaction mixture was stirred at −78° C. for 30 minutes, then at room temperature for 1 h. Water was added and the tetrahydrofuran was removed in vacuo. The aqueous residue was extracted with ether (3×100 ml) and the combined organic phases were washed with water (100 ml) and dried over sodium sulfate. The solvent was removed in vacuo to afford the title compound as a yellow oil (2.73 g).

TLC $R_f$ 0.75 (20% ethyl acetate in hexane)

INTERMEDIATE 6

2-Methanesulfonyl-7-methoxybenzofuran

A solution of Oxone® (7.37 g) in water (40 ml) was added to a solution of 7-methoxy-2-methylsulfanylbenzofuran (2.24 g) and the reaction mixture was stirred at room temperature overnight. The methanol was removed in vacuo and the resulting slurry was extracted with ethyl acetate (2×200 ml). The combined organic phases were washed with brine (200 ml) and then dried over sodium sulfate. The solvent was removed in vacuo to furnish the title compound as a yellow solid (2.24 g).

TLC $R_f$ 0.26 (20% ethyl acetate in hexane)

INTERMEDIATE 7

7-Methoxybenzofuran-2-sulfonic Acid Dimethylamide

N-Chlorosuccinimide (1 g) was added portionwise to 7-methoxybenzofuran-2-sulfinic acid, lithium salt (1.47 g) in dichloromethane (15 ml) at 0–5° C. under an inert atmosphere. The reaction was stirred at this temperature for 15 minutes and then warmed to ambient temperature and stirred for a further 15 minutes. The mixture was then flushed through a pad of celite, washing well with dichloromethane. The solvent was removed in vacuo to give a tan solid as the crude intermediate. This intermediate was added to a stirred solution of dimethylamine hydrochloride (0.67 g) and triethylamine (2.2 ml) in tetrahydrofuran (20 ml) at 0–5° C. under an inert atmosphere. The reaction was stirred at this temperature for 1 h and then warmed to room temperature and stirred for a further 48 h. The solvent was removed in vacuo and the residue partitioned between ethyl acetate (2×40 ml) and water (50 ml). The combined organic phases were washed with 1M hydrochloric acid (2×20 ml), dried over magnesium sulfate and concentrated in vacuo. The residue was washed with hexane (40 ml) to give the title compound as a tan solid (0.88 g).

TLC $R_f$0.52 (50% ethyl acetate in hexane)

INTERMEDIATE 8

(4-Bromo-7-methoxybenzofuran-2-yl)-cyclopropyl-methanone

N-bromosuccinimide (0.21 g) was added in a single portion to a stirred solution of cyclopropyl-(7-methoxybenzofuran-2-yl)-methanone (0.25 g) in acetonitrile (20 ml) under an atmosphere of nitrogen. The reaction mixture was stirred at room temperature for 24 h. Water (20 ml) was added, the mixture extracted with ethyl acetate (100 ml), the organic layer separated, dried over magnesium sulfate, filtered and concentrated in vacuo. Purification by flash chromatography on silica eluting with 5–10% ethyl acetate in hexane afforded the title compound as an off-white solid (0.24 g).

TLC $R_f$0.48 (20% ethyl acetate in hexane)

The following Intermediates were prepared using the above method.

INTERMEDIATE 9

4-Bromo-2-(cyclopropyl-methoxy-methyl)-7-methoxybenzofuran

Prepared from 2-(cyclopropyl-methoxy-methyl)-7-methoxybenzofuran (3.12 g) and N-bromosuccinimide (2.4 g) in acetonitrile (45 ml). The title compound was obtained as an orange gum (3.49 g).

TLC $R_f$0.31 (50% dichloromethane in hexane)

INTERMEDIATE 10

4-Bromo-7-methoxybenzofuran-2-sulfonic Acid Dimethylamide

Prepared from 7-methoxybenzofuran-2-sulfonic acid dimethylamide (0.82 g) and N-bromosuccinimide (0.57 g) in acetonitrile (50 ml). Purification by column chromatography eluting with 50% ethyl acetate in hexane afforded the desired product as a pale yellow solid (1.0 g).

TLC $R_f$0.34 (50% ethyl acetate in hexane).

INTERMEDIATE 11

4-Bromo-2-methanesulfonyl-7-methoxybenzofuran

Prepared from 2-methanesulfonyl-7-methoxybenzofuran (0.50 g) and N-bromosuccinimide (0.39 g) in acetonitrile (30 ml). Purification by flash chromatography on silica eluting with 50% ethyl acetate in hexane gave the title compound as a white solid (0.73 g).

TLC $R_f$0.27 (20% ethyl acetate in hexane)

INTERMEDIATE 12

2-Cyclopropanecarbonyl-7-methoxybenzofuran-4-carboxylic Acid

To a solution of (4-bromo-7-methoxybenzofuran-2-yl)-cyclopropyl-methanone (1.0 g) in tetrahydrofuran/water (40 ml/20 ml) was added palladium acetate (76 mg), 1,3-bis(diphenylphosphino)propane (280 mg) and triethylamine (4.7 ml). The reaction mixture was heated at 90° C. under a 150 psi atmosphere of carbon monoxide for 3 days. The reaction mixture was allowed to cool to room temperature and the carbon monoxide pressure released. The tetrahydrofuran was removed in vacuo and the aqueous residue washed with ethyl acetate (2×75 ml) and acidified to pH3 with 2M hydrochloric acid. The latter was extracted with ethyl acetate (2×200 ml), the organic layer separated, dried over magnesium sulfate, filtered and concentrated in vacuo to afford the title compound as a pale yellow solid (0.76 g).

TLC $R_f$0.35 (50% ethyl acetate in hexane)

The following Intermediates were prepared using the above method.

INTERMEDIATE 13

2-(Cyclopropyl-methoxy-methyl)-7-methoxybenzofuran-4-carboxylic Acid

Prepared from 4-bromo-2-(cyclopropyl-methoxy-methyl)-7-methoxy-benzofuran (350 mg), palladium acetate (25 mg), 1,3-(diphenylphosphino)propane (93 mg) and triethylamine (1.6 ml) in tetrahydrofuran/water (20 ml/10 ml). The title compound was obtained as a cream solid (250 mg).

TLC $R_f$0.10 (20% ethyl acetate in hexane

INTERMEDIATE 14

2-Dimethylsulfamyl-7-methoxybenzofuran-4-carboxylic Acid

Prepared from 4-bromo-7-methoxybenzofuran-2-sulfonic acid dimethylamide (1.0 g), triphenylphosphine (0.28 g), bis(triphenylphosphine)palladium (II) chloride (0.15 g) and triethylamine (4.2 ml) in tetrahydrofuran/water (40 ml/20 ml). The title compound was obtained as a white solid (0.79 g).

TLC $R_f$0.57 (10% methanol in dichloromethane).

INTERMEDIATE 15

2-Methanesulfonyl-7-methoxybenzofuran-4-carboxylic Acid

Prepared from 4-bromo-2-methanesulfonyl-7-methoxybenzofuran (1.64 g), triphenylphosphine (0.49 g), bis(triphenylphosphine)palladium (II) chloride (0.25 g) and triethylamine (7.2 ml) in tetrahydrofuran/water (68 ml/35 ml). The title compound was obtained as a white solid (1.23 g).

TLC $R_f$0.21 (ethyl acetate)

INTERMEDIATE 16

2-Cyclopropanecarbonyl-7-methoxybenzofuran-4-carboxylic Acid 4-nitrophenyl Ester To a stirred suspension of 2-cyclopropanecarbonyl-7-methoxybenzofuran-4-carboxylic acid (0.50 g) in dichloromethane (30 ml) under an atmosphere of nitrogen was added 4-nitrophenol (0.29 g), 4-dimethylaminopyridine (20 mg) and 1-(3-dimethylaminopropyl)-3-ethylcarbodiimide hydrochloride (0.41 g). The reaction mixture was stirred at room temperature for 18 h. Water (30 ml) was added and the mixture extracted with dichloromethane (150 ml). The organic layer was separated, dried over magnesium sulfate, filtered and concentrated in vacuo. Purification by flash chromatography on silica eluting with 40% ethyl acetate in hexane afforded the title compound as a pale yellow solid (0.59 g).

TLC $R_f$ 0.31 (40% ethyl acetate in hexane)

The following Intermediates were prepared using the above method.

INTERMEDIATE 17

2-Cyclopropyl-methoxy-methyl)-7-methoxybenzofuran-4-carboxylic Acid 4-nitrophenyl Ester Prepared from 2-(cyclopropyl-methoxy-methyl)-7-methoxybenzofuran-4-carboxylic acid (250 mg), 4-nitrophenol (140 mg), 4-dimethylaminopyridine (11 mg) and 1-(3-dimethylaminopropyl)-3-ethylcarbodiimide hydrochloride (190 mg) in dichloromethane (20 ml). The title compound was obtained as a pale yellow oil (230 mg).

TLC $R_f$ 0.24 (20% ethyl acetate in hexane)

INTERMEDIATE 18

2-Dimethylsulfamyl-7-methoxybenzofuran-4-carboxylic Acid 4-nitrophenyl Ester

Prepared from 2-dimethylsulfamyl-7-methoxybenzofuran-4-carboxylic acid (0.5 g), 4-nitrophenol (270 mg), 4-dimethylaminopyridine (11 mg) and 1-(3-dimethylaminopropyl)-3-ethylcarbodiimide hydrochloride (370 mg) in dichloromethane (30 ml). Trituration from ethyl acetate and hexane afforded the desired product as a cream solid (0.61 g).

TLC $R_f$ 0.79 (ethyl acetate)

INTERMEDIATE 19

7-Methoxy-2-(1-methyl-piperidin-4-yloxymethyl)-benzofuran-4-carboxylic Acid 4-nitrophenyl Ester Prepared from 7-methoxy-2-(1-methyl-piperidin-4-yloxymethyl)-benzofuran-4-carboxylic acid (1.9 g), 4-nitrophenol (835 mg), 1-(3-dimethylaminopropyl)-3-ethylcarbodiimide hydrochloride (1.15 g) and 4-dimethylaminopyridine (catalytic amount) in dichloromethane (40 ml). Purification by column chromatography eluting with 10% methanol in dichloromethane afforded the desired product as a pale yellow solid (720 mg).

TLC $R_f$ 0.30 (10% methanol in dichloromethane).

INTERMEDIATE 20

2-Cyclopropanecarbonyl-7-methoxybenzofuran-4-carboxylic Acid (3-methylpyridin-4-yl)amide To a stirred solution of 4-amino-3-methylpyridine (160 mg) in dimethylformamide (10 ml) under an atmosphere of nitrogen was added sodium hexamethyldisilazide (1.0M solution in tetrahydrofuran, 1.5 ml). The reaction mixture was stirred at room temperature for 10 minutes. 2-Cyclopropanecarbonyl-7-methoxy-benzofuran-4-carboxylic acid 4-nitrophenyl ester (280 mg) was then added and stirring continued for 18 h. Water (10 ml) was added and the solvent was removed in vacuo. The residue was dissolved in ethyl acetate (150 ml), washed with water (3×50 ml) and washed with brine (50 ml). The combined aqueous layers were extracted with dichloromethane (2×50 ml), the organic layers were combined, dried over magnesium sulfate, filtered and concentrated in vacuo. Purification by flash chromatography on silica eluting with 5% methanol in dichloromethane followed by trituration with diethyl ether afforded the title compound as an off-white solid (130 mg).

TLC $R_f$ 0.21 (5% methanol in dichloromethane)

INTERMEDIATE 21

2-Cyclopropanecarbonyl-7-methoxybenzofuran-4-carboxylic Acid (3-methyl-1-oxy-pyridin-4-yl)amide To a stirred solution of 2-cyclopropanecarbonyl-7-methoxybenzofuran-4-carboxylic acid (3-methylpyridin-4-yl)amide (120 mg) in chloroform (10 ml) was added peracetic acid (36–40% solution in acetic acid, 1.13 ml). The reaction mixture was stirred at room temperature for 72 h. The solvent was removed in vacuo and the residue washed with water (5 ml) and diethyl ether (5 ml) to afford the title compound as a pale yellow solid (106 mg).

TLC $R_f$ 0.24 (10% methanol in dichloromethane)

INTERMEDIATE 22

2-(2-Formyl-6-methoxyphenoxy)acetaldehyde, Dimethyl Acetal o-Vanillin (20 g) and potassium carbonate (18 g) were stirred in N,N-dimethylformamide (80 ml) at room temperature for 30 minutes. Bromoacetaldehyde dimethylacetal (24 g) was added dropwise ensuring that the temperature did not rise above 50° C. The mixture was then heated at reflux for 4 h then cooled to room temperature. Diethyl ether (30 ml) was added and the mixture was filtered. The solid was washed with ether (2×30 ml) and the combined organic phases were concentrate din vacuo to give the title compound (33 g) as a green oil.

TLC $R_f$ 0.66 (50% ethyl acetate in hexane)

INTERMEDIATE 23

2-Formyl-7-methoxybenzofuran 2-(2-Formyl-6-methoxyphenoxy)acetaldehyde, dimethyl acetal (31 g) was heated to reflux in glacial acetic acid (120 ml) overnight. The mixture was then cooled and the solvent removed in vacuo to give a red oil. Purification by Kugelrohr distillation gave the title compound (17 g) as a pale yellow oil which solidified on standing.

TLC $R_f$ 0.71 (dichloromethane)

INTERMEDIATE 24

2-Formyl-4-bromo-7-methoxybenzofuran

2-Formyl-7-methoxybenzofuran (1.0 g) was stirred in dichloromethane (10 ml) under nitrogen at 0° C. Sodium acetate (1.4 g) was added followed by the dropwise addition of bromine (0.29 ml). Further dichloromethane (20 ml) was added to the mixture to facilitate stirring and the mixture was stirred overnight. The reaction mixture was diluted with dichloromethane (40 ml) and washed with water (30 ml). Drying over magnesium sulfate followed by removal of the solvent in vacuo gave a pale orange solid. Purification by flash chromatography on silica eluting with 10% ethyl acetate in hexane gave the title compound (0.50 g) as a beige solid.

TLC $R_f$ 0.30 (10% ethyl acetate in hexane)

INTERMEDIATE 25

(4-Bromo-7-methoxybenzofuran-2-yl)-methanol

Sodium borohydride (1.12 g) was added portionwise to a stirred solution of 2-formyl-4-bromo-7-methoxybenzofuran (30 g) in 1-butanol (150 ml) at ambient temperature. After stirring for 1 h the reaction was quenched by the addition of 2M hydrochloric acid (100 ml) and stirred overnight. The mixture was separated and the organic phase washed with water (200 ml). The combined aqueous phases were extracted with tert-butyl methyl ether (100 ml). The organic phases were combined and concentrated in vacuo followed by drying in vacuo at 60° C. to afford the title compound as a brown solid (26 g).

TLC $R_f$ 0.15 (25% ethyl acetate in hexane).

INTERMEDIATE 26

4-Bromo-2-bromomethyl-7-methoxy-benzofuran

Carbon tetrabromide (1.52 g) was added to a stirred solution of (4-bromo-7-methoxybenzofuran-2-yl)-methanol (1 g) in dichloromethane (10 ml) at 0° C. under an inert atmosphere. Triphenylphosphine (1.53 g) was then added and the reaction stirred for 1 h. The reaction mixture was preadsorbed onto silica and purified by column chromatography eluting with 25% ethyl acetate in hexane to afford the title compound as a yellow solid (0.78 g).

TLC $R_f$ 0.45 (25% ethyl acetate in hexane).

INTERMEDIATE 27

4-(4-Bromo-7-methoxybenzofuran-2-ylmethoxy)-piperidine-1-carboxylic Acid tert-butyl Ester Sodium hydride (72 mg of a 60% dispersion in oil) was added to a stirred solution of 4-hydroxy-piperidine-1-carboxylic acid tert-butyl ester (363 mg) in N,N-dimethylformamide (10 ml) under an inert atmosphere at ambient temperature. After stirring for 30 minutes 4-bromo-2-bromomethyl-7-methoxybenzofuran (526 mg) was added and the reaction stirred overnight. The reaction mixture was preadsorbed onto silica and purified by column chromatography eluting with 25% ethyl acetate in hexane to afford the desired product as a yellow oily solid (269 mg).

TLC $R_f$ 0.33 (25% ethyl acetate in hexane).

INTERMEDIATE 28

4-(4-Bromo-7-methoxybenzofuran-2-ylmethoxy)-piperidine

Trifluoroacetic acid (5 ml) was added to a stirred solution of 4-(4-bromo-7-methoxybenzofuran-2-ylmethoxy)-piperidine-1-carboxylic acid tert-butyl ester (1.3 g) in dichloromethane (50 ml). After stirring at room temperate overnight the reaction was diluted with dichloromethane (150 ml) washed with 1M sodium hydroxide (100 ml) and dried over magnesium sulfate. The organic phase was concentrated in vacuo to afford the title compound as a pale yellow gum (0.98 g).

Mass spectrum 340 [M+H]$^+$.

INTERMEDIATE 29

4-(4-Bromo-7-methoxybenzofuran-2-ylmethoxy)-1-methyl-piperidine 4-(4-Bromo-7-methoxybenzofuran-2-ylmethoxy)-piperidine (0.98 g), formic acid (0.65 ml) and formaldehyde (0.56 g of a 37% w/w solution in water) were combined and heated to 95° C. overnight. After cooling to room temperature the mixture was diluted with water (70 ml) and a concentrated aqueous solution of sodium hydroxide added until the solution was basic (pH=14). It was extracted with ethyl acetate (2×100 ml). The combined organic extracts were dried over magnesium sulfate and concentrated in vacuo to afford the title compound as a pale yellow oil (1.03 g).

Mass spectrum 355 [M+H]$^+$.

INTERMEDIATE 30

7-Methoxy-2-(1-methyl-piperidin-4-yloxymethyl)-benzofuran-4-carboxylic Acid 4-(4-Bromo-7-methoxy-benzofuran-2-ylmethoxy)-1-methyl-piperidine (1 g), bis(triphenylphosphine)palladium chloride (142 mg), triphenylphosphine (300 mg), triethylamine (5 ml), tetrahydrofuran (12 ml) and water (4 ml) were combined in a Parr pressure reactor and heated to 90° C. under 140 psi of carbon monoxide for 3 days. After cooling to room temperature and releasing the pressure, the mixture was diluted with water (100 ml) and washed with ethyl acetate (2×100 ml). The aqueous layer was acidified with concentrated hydrochloric acid to pH5. The water was evaporated in vacuo to afford a yellow solid (1.91 g) which comprised the title compound and triethylamine hydrochloride.

Mass spectrum 320 [M+H]$^+$.

EXAMPLE 1

2-Dimethylsulfamyl-7-methoxybenzofuran-4-carboxylic Acid (3-methyl-pyridin-4-yl)amide To a stirred solution of 4-amino-3-methylpyridine (200 mg) in dimethylformamide (8 ml) under an atmosphere of nitrogen at 0° C. was added sodium hexamethyldisilazide (1.0M solution in tetrahydrofuran, 1.9 ml). The reaction mixture was stirred at this temperature for 5 minutes. 2-Dimethylsulfamyl-7-methoxy-benzofuran-4-carboxylic acid 4-nitrophenyl ester (400 mg) was then added and stirring continued for 30 minutes. Water (10 ml) was added and the solvent was removed in vacuo. The residue was dissolved in ethyl acetate (150 ml), washed with water (3×50 ml) and washed with brine (50 ml). The combined organic layers were dried over magnesium sulfate, filtered and concentrated in vacuo. Purification by column chromatography eluting with 10% methanol in ethyl acetate afforded the title compound as a white solid (0.3 g).

TLC $R_f$ 0.47 (10% methanol in ethyl acetate).

mp 216–217° C.

EXAMPLE 2

2-(Cyclopropyl-methoxy-methyl)-7-methoxybenzofuran-4-carboxylic Acid (3,5-dichloro-1-oxy-pyridin-4-yl)amide To a stirred solution of 4-amino-3,5-dichloro-1-oxy-piperidine (960 mg) in dimethylformamide (40 ml) under an atmosphere of nitrogen and added sodium hydride (60% dispersion in mineral oil, 236 mg). The reaction mixture was stirred at room temperature for 10 minutes. 2-Cyclopropyl-methoxy-methyl)-7-methoxy-benzofuran-4-carboxylic acid 4-nitrophenyl ester (710 mg) was then added and stirring continued for 90 minutes. Water (5 ml) was added and the solvent was removed in vacuo. The resulting residue was purified by flash chromatography on silica eluting with ethyl acetate affording the title compound as an orange solid (47 mg).

TLC $R_f$ 0.18 (ethyl acetate)

mp 162–164° C. (dec.)

The following compound was prepared by a similar procedure.

EXAMPLE 3

7-Methoxy-2-(1-methyl-piperidin-4-yloxymethyl)-benzofuran-4-carboxylic Acid (3,5-dichloro-1-hydroxy-pyridin-4-yl)-amide Prepared from sodium hydride (115 mg of a 60% dispersion in oil), 4-amino-3,5-dichloropyridine-N-oxide (474 mg), 7-methoxy-2-(1-methyl-piperidin-4-yloxymethyl)-benzofuran-4-carboxylic acid 4-nitrophenyl ester (389 mg) in N,N-dimethylformamide. Purification by column chromatography eluting with 20% methanol in dichloromethane afforded the desired product as a light brown solid (106 mg).

TLC $R_f$ 0.23 (20% methanol in dichloromethane).

Mass spectrum 481 $[M+H]^+$.

EXAMPLE 4

2-Methanesulfonyl-7-methoxybenzofuran-4-carboxylic Acid (3-methylpyridin-4-yl)amide Oxalyl chloride (0.27 ml) was added to 2-methanesulfonyl-7-methoxybenzofuran-4-carboxylic acid (0.40 g) in dichloromethane (15 ml) under an inert atmosphere. Dimethylformamide (catalytic amount) was added and the reaction mixture stirred at room temperature overnight. The solvent was removed in vacuo to furnish the corresponding acid chloride as a yellow solid. 4-Amino-3-methylpyridine (0.32 g) was added to the acid chloride in dichloromethane (30 ml). The reaction mixture was stirred at room temperature overnight and then the solvent was removed in vacuo. The crude product was purified by flash chromatography on silica eluting with 10% methanol in ethyl acetate to afford the title compound as an off-white solid (0.38 g).

TLC $R_f$ 0.2 (10% methanol in ethyl acetate)

mp 191–193° C.

EXAMPLE 5

2-Dimethylsulfamyl-7-methoxybenzofuran-4-carboxylic Acid (3-methyl-1-oxy-pyridin-4-yl)amide To a stirred solution of 2-dimethylsulfamyl-7-methoxybenzofuran-4-carboxylic acid (3-methyl-pyridin-4-yl)amide (0.16 g) in chloroform (15 ml) was added peracetic acid (36–40% solution in acetic acid, 0.08 ml). The reaction was stirred at room temperature overnight. The solvent was removed in vacuo and the residue purified by column chromatography eluting with 10% methanol in dichloromethane to afford the desired compound as a white solid (0.14 g).

TLC $R_f$ 0.36 (10% methanol in dichloromethane)

mp 186–187° C.

The following Example was prepared by a similar procedure.

EXAMPLE 6

2-Methanesulfonyl-7-methoxybenzofuran-4-carboxylic Acid (3-methyl-1-oxy-pyridin-4-yl)amide Prepared from 2-methanesulfonyl-7-methoxybenzofuran-4-carboxylic acid (3-methylpyridin-4-yl)amide (0.20 g). The title compound was obtained as a white solid (0.17 g).

TLC $R_f$ 0.4 (50% methanol in ethyl acetate)

mp 171–173° C.

EXAMPLE 7

2-(Cyclopropyl-hydroxy-methyl)-7-methoxybenzofuran-4-carboxylic Acid (3-methyl-1-oxy-pyridin-4-yl)amide To a stirred suspension of 2-cyclopropanecarbonyl-7-methoxybenzofuran-4-carboxylic acid (3-methyl-1-oxy-pyridin-4-yl)amide (50 mg) in methanol (10 ml) cooled to 0° C. was added portionwise sodium borohydride (20 mg). The reaction mixture was allowed to warm to room temperature and stirred for 10 minutes. Water (5 ml) was added and the methanol removed in vacuo. The aqueous residue was extracted with dichloromethane (2×100 ml), the organic layer separated, dried over magnesium sulfate, filtered and concentrated in vacuo. Trituration with diethyl ether afforded the title compound as a white solid (28 mg).

TLC $R_f$ 0.32 (15% methanol in dichloromethane)

mp 207–209° C. (dec.)

Assay Methods

The assays used to confirm the phosphodiesterase IV inhibitory activity of compounds of formula (1) are standard assay procedures as disclosed by Schilling et al, Anal. Biochem. 261:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV-related disease states in those assays.

The ability of compounds of formula (i) to inhibit TNF production in human peripheral blood mononuclear cells (PMBC's) is measured as follows. PMBC's are prepared from freshly taken blood or "Buffy coats" by standard procedures. Cells are plated out in RPMI1640+1% foetal calf serum in the presence and absence of inhibitors. LPS (100 ng/ml) is added and cultures are incubated for 22 h at 37° C. in an atmosphere of 95% air/5% $CO_2$. Supernatants are tested for TNFα by ELISA using commercially available kits.

Activity in a guinea pig lung model is measured using the procedures described by Mauser et al, Am. Rev. Respir. Dis. 148 1623 (1993) and Am. J. Respir. Crit. Care Med. 152 467 (1995).

The pharmacokinetic profile of the compounds of the invention is determined in rats cannulated in the right carotid artery for blood collection. For iv dosing, the compound is prepared in a suitable formulation, for example 10% v/v DMSO, 50% v/v PEG 400 in water, and dosing is carried out by cannulation of the left jugular vein. Samples are collected at 5 min. 0.5, 1, 2, 4, 6 and 8 hours post-dosing. For oral dosing, the compound is prepared in a suitable formulation such as 0.4% w/v methylcellulose in water. Samples are collected at 0.5, 1, 2, 4, 6 and 8 hours post-dosing. In some cases, samples are also collected at 12 hours post-dosing. Plasma is obtained by centrifugation of the each blood sample and drug concentration is then determined using standard methods, such as liquid chromatography-mass spectrometry following protein precipitation.

Abbreviations

LPS Lipopolysaccharide (endotoxin)

ELISA Enzyme linked immunosorbent assay

What is claimed is:

1. A compound of formula (i)

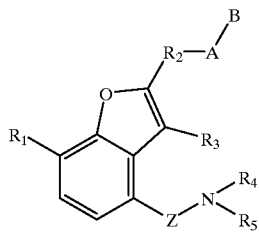

wherein

Z is CO or CS;

$R_1$ is selected from the group consisting of OH, alkoxy optionally substituted with one or more halogens, and thioalkyl optionally substituted with one or more halogens;

$R_3$ is selected from the group consisting of H, alkyl, and halogen;

$R_4$ is H or alkyl;

$R_5$ is aryl or heteroaryl, either of which may be substituted at any position with one or more substitutents $R_{14}$ or alkyl-$R_{14}$;

$R_{14}$ is selected from the group consisting of alkyl optionally substituted with one or more halogens, aryl, heteroaryl, heterocyclo, $CO_2R_8$, $CONR_9R_{10}$, $SO_2NR_9R_{10}$, $OR_{11}$, halogen, CN, $NR_8R_{12}$, $COR_{13}$, $S(O)_pR_{13}$, and $NHSO_2CF_3$;

p is 0–2;

$R_8$ is selected from the group consisting of H, alkyl, cycloalkyl, aryl, heteroaryl, heterocyclo, cycloalkylalkyl, arylalkyl, heteroarylalkyl, and heterocycloalkyl;

$R_9$ and $R_{10}$ are the same different and selected from the group consisting H, alkyl, cycloalkyl, aryl, heteroaryl, heterocyclo, cycloalkylalkyl, arylalkyl, heteroarylalkyl, and heterocycloalkyl, or $NR_9R_{10}$ represents a heterocyclic ring;

$R_{11}$ is selected from the group consisting of H, alkyl optionally substituted with one or more halogens, cycloalkyl, aryl, heteroaryl, heterocyclo, cycloalkylalkyl, arylalkyl, heteroarylalkyl, and heterocycloalkyl;

$R_{12}$ is selected from the group consisting of H, alkyl, cycloalkyl, aryl, heteroaryl, heterocyclo, cycloalkylalkyl, arylalkyl, heteroarylalkyl, heterocycloalkyl, alkylcarbonyl, alkoxycarbonyl, arylcarbonyl, heteroarylcarbonyl, heterocyclocarbonyl, alkylsulphonyl, arylsulphonyl, heteroarylsulphonyl, and heterocyclosulphonyl;

$R_{13}$ is selected from the group consisting of alkyl, cycloalkyl, aryl, heteroaryl, heterocyclo, cycloalkylalkyl, arylalkyl, heteroarylalkyl, and heterocycloalkyl;

$R_2$ is selected from the group consisting of alkyl, arylalkyl, cycloalkylalkyl, heteroarylalkyl, and heterocycloalkyl, any of which can be attached at any position on the alkyl portion to A and through the same different position to the benzofuran ring wherein the aryl or heteroaryl group is optionally substituted at any position by one or more substitutents $R_{14}$ or alkyl-$R_{14}$, and the cycloalkyl or heterocycloalkyl group is optionally substituted at any position with one or more substituents $R_7$ or alkyl-$R_7$, or $R_2$ is absent;

$R_7$ is selected from the group consisting of carbonyl oxygen, $CO_2R_8$, $CONR_9R_{10}$, $SO_2NR_9R_{10}$, $NR_8R_{12}$, $OR_{11}$, alkyl optionally substituted with one or more halogens, halogen, CN, $NHSO_2CH_3$, tetrazolyl, and heterocyclo;

A is selected from the group consisting of —O—, —O—$(C(R_{15})_2)_n$—, —O—$(C(R_{15})_2)_n$—C(=O)—$(C(R_{15})_2)_m$—, —O—$(C(R_{15})_2)_n$—$SO_q$—$(C(R_{15})_2)_m$—, —$NR_6$—, —$NR_6$—$(C(R_{15})_2)_n$—, —$NR_6$—$(C(R_{15})_2)_m$—C(=O)—$(C(R_{15})_2)_m$—, —$NR_6$—$(C(R_{15})_2)_n$—$SO_q$—$(C(R_{15})_2)_m$—, —$SO_q$—, —$SO_q$—$(C(R_{15})_2)_m$—, and —$SO_qNR_6$—;

$R_6$ is H or alkyl;

n is 1–4;

m is 0–4;

q is 1 or 2;

$R_{15}$ is H or alkyl; and

B is selected from the group consisting of H, a heterocyclic ring optionally substituted at any position with one or more substitutents $R_7$ or alkyl-$R_7$, and alkyl, aryl, or heteroaryl, any of which can be optionally substituted at any position with one or more substitutents $R_{14}$ or alkyl-$R_{14}$;

provided that B is H only when $R_2$ is cycloalkylalkyl and A is —O—, and that B is substituted when $R_2$ is not cycloalkylalkyl and A is selected from the group consisting of —O—, —O—$(C(R_{15})_2)_n$—, —O—$(C(R_{15})_2)_n$—C(=O)—$(C(R_{15})_2)_m$—, —$NR_6$—, —$NR_6$—$(C(R_{15})_2)_n$—, and —$NR_6$—$(C(R_{15})_2)_n$—C(=O)—$(C(R_{15})_2)_m$—;

or a N-oxide or pharmaceutically acceptable salt thereof.

2. The compound, according to claim 1, wherein Z is CO.

3. The compound, according to claim 1, wherein $R_1$ is alkoxy optionally substituted with one or more halogens.

4. The compound, according to claim 1, wherein $R_3$ is H.

5. The compound, according to claim 1, wherein $R_4$ is H.

6. The compound, according to claim 1, wherein $R_5$ is selected from the group consisting of phenyl, pyrimidinyl, pyridyl, and pyridyl-N-oxide, any of which can be substituted at any position with one or more substitutents $R_{14}$, wherein $R_{14}$ is alkyl optionally substituted with one or more halogens, halogen, or $OR_{11}$, or CN.

7. The compound, according to claim 1, wherein $R_2$ is not cycloalkylalkyl.

8. The compound, according to claim 1, wherein A is selected from the group consisting of —$NR_6$—, —$NR_6$—$(C(R_{15})_2)_n$—, —O—, and —O—$(C(R_{15})_2)_n$—.

9. The compound, according to claim 1, wherein $R_{14}$ is selected from the group consisting of alkyl optionally substituted with one or more halogens, halogen, and CN.

10. The compound, according to claim 1, selected from the group consisting of 2-dimethylsulfamyl-7-methoxybenzofuran-4-carboxylic acid (3-methylpyridin-4-yl)amide, 2-(cyclopropyl-methoxy-methyl)-7-methoxybenzofuran-4-carboxylic acid (3,5-dichloro-1-oxypyridin-4-yl) amide, 7-methoxy-2-(1-methyl-piperidin-74-yloxymethyl)-benzofuran-4-carboxylic acid (3,5-dichloro-1-hydroxy-pyridin-4-yl)-amide, 2-methanesulfonyl-7-methoxybenzofuran-4-carboxylic acid (3-methylpyridin-4-yl)amide, 2-dimethylsulfamyl-7-methoxybenzofuran-4-carboxylic acid (3-methyl-1-oxy-pyridin-4-yl)amide, 2-methanesulfonyl-7-methoxybenzofuran-4-carboxylic acid (3-methyl-1-oxy-pyridin-4-yl)amide, and 2-(cyclopropyl-hydroxy-methyl)-7-methoxybenzofuran-4-carboxylic acid (3-methyl-1-oxy-pyridin-4-yl)amide.

11. The compound, according to claim 1, in the form of a single enantiomer thereof.

12. A pharmaceutical composition for therapeutic use comprising a compound of formula (i)

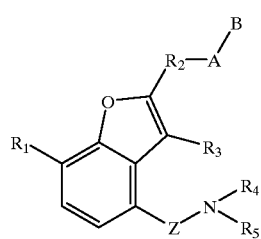

wherein
Z is CO or CS;
$R_1$ is selected from the group consisting of OH, alkoxy optionally substituted with one or more halogens, and thioalkyl optionally substituted with one or more halogens;
$R_3$ is selected from the group consisting of H, alkyl, and halogen;
$R_4$ is H or alkyl;
$R_5$ is aryl or heteroaryl, either of which may be substituted at any position with one or more substitutents $R_{14}$ or alkyl-$R_{14}$;
$R_{14}$ is selected from the group consisting of alkyl optionally substituted with one or more halogens, aryl, heteroaryl, heterocyclo, $CO_2R_8$, $CONR_9R_{10}$ $SO_2NR_9R_{10}$, $OR_{11}$, halogen, CN, $NR_8R_{12}$, $COR_{13}$, $S(O)_pR_{13}$, and $NHSO_2CF_3$;
p is 0–2;
$R_8$ is selected from the group consisting of H, alkyl, cycloalkyl, aryl, heteroaryl, heterocyclo, cycloalkylalkyl, arylalkyl, heteroarylalkyl, and heterocycloalkyl;
$R_9$ and $R_{10}$ are the same or different and selected from the group consisting H, alkyl, cycloalkyl, aryl, heteroaryl, heterocyclo, cycloalkylalkyl, arylalkyl, heteroarylalkyl, and heterocycloalkyl, or $NR_9R_{10}$ represents a heterocyclic ring;
$R_{11}$ is selected from the group consisting of H, alkyl optionally substituted with one or more halogens, cycloalkyl, aryl, heteroaryl, heterocyclo, cycloalkylalkyl, arylalkyl, heteroarylalkyl, and heterocycloalkyl;
$R_{12}$ is selected from the group consisting of H, alkyl, cycloalkyl, aryl, heteroaryl, heterocyclo, cycloalkylalkyl, arylalkyl, heteroarylalkyl, heterocycloalkyl, alkylcarbonyl, alkoxycarbonyl, arylcarbonyl, heteroarylcarbonyl, heterocyclocarbonyl, alkylsuphonyl, arylsulphonyl, heteroarylsulphonyl, and heterocyclosulphonyl;
$R_{13}$ is selected from the group consisting of alkyl, cycloalkyl, aryl, heteroaryl, heterocyclo, cycloalkylalkyl, arylalkyl, heteroarylalkyl, and heterocycloalkyl;

$R_2$ is selected from the group consisting of alkyl, arylalkyl, cycloalkylalkyl, heteroarylalkyl, and heterocycloalkyl, any of which can be attached at any position on the alkyl portion to A and through the same or different position to the benzofuran ring wherein the aryl or heteroaryl group is optionally substituted at any position by one or more substitutents $R_{14}$ or alkyl-$R_{14}$, and the cycloalkyl or heterocycloalkyl group is optionally substituted at any position with one or more substitutents $R_7$ or alkyl-$R_7$, or $R_2$ is absent;

$R_7$ is selected from the group consisting of carbonyl oxygen, $CO_2R_8$, $CONR_9R_{10}$, $SO_2NR_9R_{10}$, $NR_8R_{12}$, $OR_{11}$, alkyl optionally substituted with one or more halogens, halogen, CN, $NHSO_2CF_3$, tetrazolyl, and heterocyclo;

A is selected from the group consisting of —O—, —O—$(C(R_{15})_2)_n$—, —O—$(C(R_{15})_2)_n$—$C(=O)$—$(C(R_{15})_2)_m$—, —O—$(C(R_{15})_2)_n$—$SO_q$—$(C(R_{15})_2)_m$—, —$NR_6$—, —$NR_6$—$(C(R_{15})_2)_n$—, —$NR_6$—$(C(R_{15})_2)_n$—$C(=O)$—$(C(R_{15})_2)_m$—, —$NR_6$—$(C(R_{15})_2)_n$—$SO_q$—$(C(R_{15})_2)_m$—, —$SO_q$—, $SO_q$—$(C(R_{15})_2)_m$—, and —$SO_qNR_6$—;

$R_6$ is H or alkyl;
n is 1–4;
m is 0–4;
q is 1 or 2;
$R_{15}$ is H or alkyl; and
B is selected from the group consisting of H, a heterocyclic ring optionally substituted at any position with one or more substitutents $R_7$ or alkyl-$R_7$, and alkyl, aryl, or heteroaryl, any of which can be optionally substituted at any position with one or more substituents $R_{14}$ or alkyl-$R_{14}$;

provided that B is H only when $R_2$ is cycloalkylalkyl and A is —O—, and that B is substituted when $R_2$ is not cycloalkylalkyl and A is selected from the group consisting of —O—, —O—$(C(R_{15})_2)_n$, —O—$(C(R_{15})_2)_n$—$C(=O)$—$(C(R_{15})_2)_m$—, —$NR_6$—, —$NR_6$—$(C(R_{15})_2)_n$—, and —$NR_6$—$(C(R_{15})_2)_n$—$C(=O)$—$(C(R_{15})_2)_m$—;

or a N-oxide or pharmaceutically acceptable salt thereof, and a pharmaceutically-acceptable carrier or excipient.

13. A method for the inhibition of phosphodiesterase IV, Tumour Necrosis Factor, or eosinophil accumulation, wherein said method comprises the administration of an effective amount of a compound of formula (i)

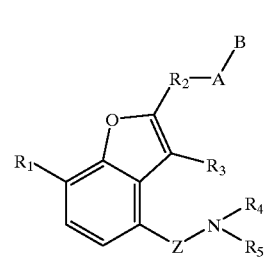

wherein
Z is CO or CS;
$R_1$ is selected from the group consisting of OH, alkoxy optionally substituted with one or more halogens, and thioalkyl optionally substituted with one or more halogens;
$R_3$ is selected from the group consisting of H, alkyl, and halogen;

$R_4$ is H or alkyl;

$R_5$ is aryl or heteroaryl, either of which may be substituted at any position with one or more substitutents $R_{14}$ or alkyl-$R_{14}$;

$R_{14}$ is selected from the group consisting of alkyl (optionally substituted with one or more halogens), aryl, heteroaryl, heterocyclo, $CO_2R_8$, $CONR_9R_{10}$, $SO_2NR_9R_{10}$, $OR_{11}$, halogen, CN, $NR_8R_{12}$, $COR_{13}$, $S(O)_pR_{13}$, and $NHSO_2CF_3$;

p is 0–2;

$R_8$ is selected from the group consisting of H, alkyl, cycloalkyl, aryl, heteroaryl, heterocyclo, cycloalkylalkyl, arylalkyl, heteroarylalkyl, and heterocycloalkyl;

$R_9$ and $R_{10}$ are the same or different and selected from the group consisting H, alkyl, cycloalkyl, aryl, heteroaryl, heterocyclo, cycloalkylalkyl, arylalkyl, heteroarylalkyl, and heterocycloalkyl, or $NR_9R_{10}$ represents a heterocyclic ring;

$R_{11}$ is selected from the group consisting of H, alkyl (optionally substituted with one or more halogens), cycloalkyl, aryl, heteroaryl, heterocyclo, cycloalkylalkyl, arylalkyl, heteroarylalkyl, and heterocycloalkyl;

$R_{12}$ is selected from the group consisting of H, alkyl, cycloalkyl, aryl, heteroaryl, heterocyclo, cycloalkylalkyl, arylalkyl, heteroarylalkyl, heterocycloalkyl, alkylcarbonyl, alkoxycarbonyl, arylcarbonyl, heteroarylcarbonyl, heterocyclocarbonyl, alkylsuphonyl, arylsulphonyl, heteroarylsulphonyl, and heterocyclosulphonyl;

$R_{13}$ is selected from the group consisting of alkyl, cycloalkyl, aryl, heteroaryl, heterocyclo, cycloalkylalkyl, arylalkyl, heteroarylalkyl, and heterocycloalkyl;

$R_2$ is selected from the group consisting of alkyl, arylalkyl, cycloalkylalkyl, heteroarylalkyl, and heterocycloalkyl, any of which can be attached at any position on the alkyl portion to A and through the same or different position to the benzofuran ring wherein the aryl or heteroaryl group is optionally substituted at any position by one or more substitutents $R_{14}$ or alkyl-$R_{14}$, and the cycloalkyl or heterocycloalkyl group is optionally substituted at any position with one or more substitutents $R_7$ or alkyl-$R_7$, or $R_2$ is absent;

$R_7$ is selected from the group consisting of carbonyl oxygen, $CO_2R_8$, $CONR_9R_{10}$, $SO_2NR_9R_{10}$, $NR_8R_{12}$, $OR_{11}$, alkyl (optionally substituted with one or more halogens), halogen, CN, $NHSO_2CF_3$, tetrazolyl, and heterocyclo;

A is selected from the group consisting of —O—, —O—$(C(R_{15})_2)_n$—, —O—$(C(R_{15})_2)_n$—C(=O)—$(C(R_{15})_2)_m$—, —O—$(C(R_{15})_2)_n$—$SO_q$—$(C(R_{15})_2)_m$—, —$NR_6$—, —$NR_6$—$(C(R_{15})_2)_n$—, —$NR_6$—$(C(R_{15})_2)_n$—C(=O)—$(C(R_{15})_2)_m$—, —$NR_6$—$(C(R_{15})_2)_n$—$SO_q$—$(C(R_{15})_2)_m$—, —$SO_q$—, $SO_q$—$(C(R_{15})_2)_m$—, and —$SO_qNR_6$—;

$R_6$ is H or alkyl;

n is 1–4;

m is 0–4;

q is 1 or 2;

$R_{15}$ is H or alkyl; and

B is selected from the group consisting of H, a heterocyclic ring optionally substituted at any position with one or more substituents $R_7$ or alkyl-$R_7$, and alkyl, aryl, or heteroaryl, any of which can be optionally substituted at any position with one or more substituents $R_{14}$ or alkyl-$R_{14}$;

provided that B is H only when $R_2$ is cycloalkylalkyl and A is —O—, and that B is substituted when $R_2$ is not cycloalkylalkyl and A is selected from the group consisting of —O—, —O—$(C(R_{15})_2)_n$, —O—$(C(R_{15})_2)_n$—C(=O)—$(C(R_{15})_2)_m$—, —$NR_6$—, —$NR_6$—$(C(R_{15})_2)_n$—, and —$NR_6$—$(C(R_{15})_2)_n$—C(=O)—$(C(R_{15})_2)_m$—;

or a N-oxide or pharmaceutically acceptable salt thereof.

* * * * *

UNITED STATES PATENT AND TRADEMARK OFFICE
CERTIFICATE OF CORRECTION

PATENT NO. : 6,066,657  
DATED : May 23, 2000  
INVENTOR(S) : Dyke et al.

Page 1 of 1

It is certified that error appears in the above-identified patent and that said Letters Patent is hereby corrected as shown below:

Column 16, claim 13,
Line 27, "alkyl-$R_7$," should read -- alkyl-$R_7$), --.

Column 21, claim 1,
Line 39, "same different" should read -- same or different --.

Column 22, claim 1,
Line 8, "$NHSO_2CH_3$" should read -- $NHSO_2CF_3$ --.
Lines 12-13, "$-NR_6-(C(R_{15})_2)_m-C(=O)-(C(R_{15})_2)_m-$" should read -- $-NR_6-(C(R_{15})_2)_n-C(=O)-(C(R_{15})_2)_m-$ --.

Column 23, claim 12,
Line 40, "$CONR_9R_{10}SO_2NR_9R_{10}$," should read -- $CONR_9R_{10}, SO_2NR_9R_{10}$, --.

Column 25, claim 13,
Line 9, "$CONR_9R_{10}SO_2NR_9R_{10}$," should read -- $CONR_9R_{10}, SO_2NR_9R_{10}$, --.

Column 26, claim 13
Line 26, "optionally" should read -- (optionally --.

Signed and Sealed this

Twelfth Day of March, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.   : 6,066,657
DATED        : May 23, 2000
INVENTOR(S)  : Dyke et al.

It is certified that error appears in the above-identified patent and that said Letters Patent is hereby corrected as shown below:

Column 16, claim 13,
Line 27, "alkyl-$R_7$," should read -- alkyl-$R_7$), --.

Column 21, claim 1,
Line 39, "same different" should read -- same or different --.

Column 22, claim 1,
Line 8, "$NHSO_2CH_3$" should read -- $NHSO_2CF_3$ --.
Lines 12-13, "–$NR_6$–$(C(R_{15})_2)_m$–C(=O)–$(C(R_{15})_2)_m$–" should read -- –$NR_6$–$(C(R_{15})_2)_n$–C(=O)–$(C(R_{15})_2)_m$– --.

Column 23, claim 12,
Line 40, "$CONR_9R_{10}SO_2NR_9R_{10}$," should read -- $CONR_9R_{10}, SO_2NR_9R_{10}$, --.

Column 25, claim 13,
Line 9, "$CONR_9R_{10}SO_2NR_9R_{10}$," should read -- $CONR_9R_{10}, SO_2NR_9R_{10}$, --.

Column 26, claim 13
Line 26, "optionally" should read -- (optionally --.

Signed and Sealed this

Nineteenth Day of March, 2002

Attest:

*Attesting Officer*

JAMES E. ROGAN
*Director of the United States Patent and Trademark Office*